(12) United States Patent
Schweers et al.

(10) Patent No.: US 6,339,175 B1
(45) Date of Patent: Jan. 15, 2002

(54) PROCESS FOR THE NON-OXIDATIVE PREPARATION OF FORMALDEHYDE FROM METHANOL

(75) Inventors: Elke Schweers, Bad Soden; Thomas Kaiser, Kelkheim; Michael Haubs, Bad Kreuznach; Michael Rosenberg, Niedernhausen, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/445,082

(22) PCT Filed: May 26, 1998

(86) PCT No.: PCT/EP98/03082

§ 371 Date: Feb. 22, 2000

§ 102(e) Date: Feb. 22, 2000

(87) PCT Pub. No.: WO98/55434

PCT Pub. Date: Dec. 10, 1998

(30) Foreign Application Priority Data

| | | | |
|---|---|---|---|
| Jun. 2, 1997 | (DE) | ............ | 197 22 774 |
| Jun. 30, 1997 | (DE) | ............ | 197 27 520 |
| Jun. 30, 1997 | (DE) | ............ | 197 27 519 |
| Sep. 30, 1997 | (DE) | ............ | 197 43 145 |
| Mar. 31, 1998 | (DE) | ............ | 198 14 283 |

(51) Int. Cl.$^7$ ............................................. C07C 45/00
(52) U.S. Cl. ..................... 568/487; 568/449; 568/485; 568/493
(58) Field of Search ........................... 568/449, 485, 568/487, 493

(56) References Cited

FOREIGN PATENT DOCUMENTS

DE  3719055  * 12/1998

OTHER PUBLICATIONS

Ruf et al, Applied Catalysis, 161 (1–2), L19–L24 (1997)—Abstract only.*
Phillippe et al, Catal. Today, 20(3), 325–34 (1994)—Abstract only.*

* cited by examiner

Primary Examiner—Sreeni Padmanabhan
(74) Attorney, Agent, or Firm—Connolly Bove Lodge & Hutz LLP

(57) ABSTRACT

In a process for preparing formaldehyde from methanol by dehydrogenation in a reactor in the presence of a catalyst at a temperature in the range from 300 to 1000° C., a carrier gas stream which has a temperature above the dehydrogenation temperature is fed to the reactor.

18 Claims, 2 Drawing Sheets

PROCESS FOR THE NON-OXIDATIVE PREPARATION OF FORMALDEHYDE FROM METHANOL

This application is the US National Stage Application of PCT/EP98/03082 filed May 26, 1998.

A number of processes for preparing formaldehyde from methanol are known (see, for example, Ullmann's Encyclopaedia of Industrial Chemistry). The processes carried out industrially are predominantly the oxidation:

$$CH_3OH + \tfrac{1}{2}O_2 \rightarrow CH_2O + H_2O$$

over catalysts comprising iron oxide and molybdenum oxide at from 300° C. to 450° C. (Formox process) and the oxidative dehydrogenation (silver catalyst process) according to:

$$CH_3OH \rightarrow CH_2O + H_2$$

$$H_2 + \tfrac{1}{2}O_2 \rightarrow H_2O$$

at from 600° C. to 720° C. In both processes, the formaldehyde is first obtained as an aqueous solution. Particularly when used for the preparation of formaldehyde polymers and oligomers, the formaldehyde obtained in this way has to be subjected to costly dewatering. A further disadvantage is the formation of corrosive formic acid, which has an adverse effect on the polymerization, as by-product.

The dehydrogenation of methanol enables these disadvantages to be avoided and enables, in contrast to the abovementioned processes, virtually water-free formaldehyde to be obtained directly:

$$CH_3OH \xrightarrow{cat.} CH_2O + H_2$$

In order to achieve an ecologically and economically interesting industrial process for the dehydrogenation of methanol, the following prerequisites have to be met: the strongly endothermic reaction should be carried out at high temperatures so that high conversions are achieved. Competing secondary reactions have to be suppressed in order to achieve sufficient selectivity for formaldehyde (without catalysis, the selectivity for the formation of formaldehyde is less than 10% at conversions above 90%). The residence times have to be short or the cooling of the reaction products has to be rapid in order to minimize the decomposition of the formaldehyde which is not thermodynamically stable under the reaction conditions $$CH_2O \rightarrow CO + H_2.$$

Various methods of carrying out this reaction have been proposed; thus, for example, DE-A-37 19 055 describes a process for preparing formaldehyde from methanol by dehydrogenation in the presence of a catalyst at elevated temperature. The reaction is carried out in the presence of a catalyst comprising at least one sodium compound at a temperature of from 300° C. to 800° C.

J. Sauer and G. Emig (Chem. Eng. Technol. 1995, 18, 284–291) were able to set free a catalytically active species, which they presumed to be sodium, from a catalyst comprising $NaAlO_2$ and $LiAlO_2$ by means of a reducing gas mixture (87% $N_2$+13% $H_2$). The species was able to catalyze the dehydrogenation of methanol introduced at a downstream point in the same reactor, i.e. not coming into contact with the catalyst bed, to give formaldehyde. When using non-reducing gases, only a low catalytic activity was observed.

According to J. Sauer and G. Emig and also results from more recent studies (see, for example, M. Bender et al., paper presented to the 30th annual meeting of German catalyst technologists, Mar. 21–23, 1997), sodium atoms and NaO molecules were identified as species emitted into the gas phase and their catalytic activity for the dehydrogenation of methanol in the gas phase was described. In the known processes, the starting material methanol is always diluted with nitrogen and/or nitrogen/hydrogen mixtures for the reaction.

Although good results are achieved with the known processes, there is nevertheless considerable room for improvement from a technical and economic point of view, particularly because the catalysts employed become exhausted or inactivated over time and the formaldehyde yields are still capable of improvement.

It has surprisingly been found that the yield in the dehydrogenation can be increased if a carrier gas stream which has been brought to a temperature above the actual reaction temperature by heating is introduced into the reactor. By means of such a superheated carrier gas stream, at least part of the heat required for the endothermic dehydrogenation reactor can be introduced.

An advantage here is that the heat of reaction does not have to be transferred to the gas stream via a hot wall, i.e. one having a temperature above the reaction temperature, in the reaction zone, but can be introduced directly and more gently for the reaction gases by means of the separate heating and intensive mixing of the various substreams. Decomposition of the unstable formaldehyde and secondary reactions at the high temperatures in the reactor, in particular in the zones close to the wall, can thus be reduced.

The invention accordingly provides a process for preparing formaldehyde from methanol by dehydrogenation in a reactor in the presence of a catalyst at a temperature in the range from 300 to 1000° C., wherein a carrier gas stream which has a temperature above the dehydrogenation temperature is fed to the reactor.

The temperature difference between carrier gas stream and dehydrogenation temperature is preferably at least 20° C., particularly preferably from 40 to 250° C.

The superheated gas stream can be fed directly into the reaction zone or all or part of it can be brought into contact with a primary catalyst (see below) beforehand.

The preferred temperatures for the superheated gas stream are from 600 to 1000° C., particularly preferably from 700 to 900° C. Preferred temperatures for the dehydrogenation of the methanol are from 500 to 900° C.; particular preference is given to temperatures of from 600 to 800° C.

The carrier gas stream or streams can consist of a reducing or non-reducing gas, for example $H_2/CO$ mixtures or nitrogen, preferably the by-products of the dehydrogenation.

Figure 1:
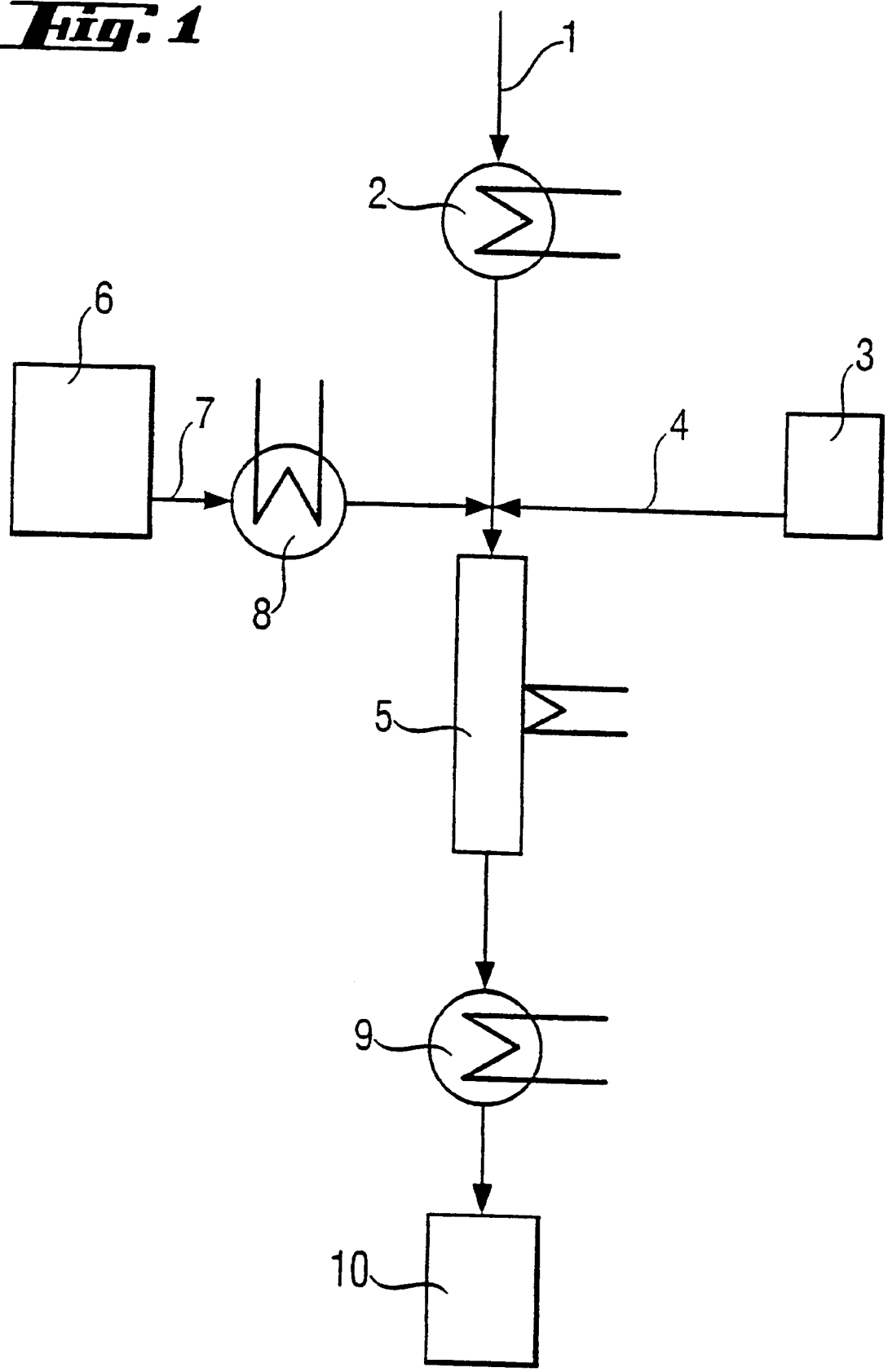
FIG. 1 shows a schematic overview of a preferred variant of the process of the invention.

The carder gas stream 1 is heated in the heat exchanger 2. Together with the catalyst 4 coming from a reservoir 3, the total stream is introduced into the reactor 5. Methanol 7 is conveyed from a reservoir 6, vaporized in a heat exchanger 8 and likewise fed to the reactor 5. The product gases from the reactor 5 are cooled in the heat exchanger 9 and fed to a unit 10 for separating off the formaldehyde.

The invention further provides an apparatus for carrying out the abovementioned process comprising one or more heat exchangers for preheating the starting materials, a vessel for superheating a carrier gas stream, a heated reactor for carrying out the dehydrogenation, one or more heat exchangers for cooling the product mixture, a unit for separating off the formaldehyde and an apparatus for introduction of the methanol and for further introduction of a catalyst For the purposes of the invention, dehydrogenation is a non-oxidative process according to the equation:

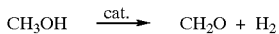

Suitable catalysts are known, for example, from the literature, sees for example, Chem, Eng. Technol. 1994, 17, 34.

Suitable metals are, for example, Li, Na, K, Cs, Mg, Al, In, Ga, Ag, Cu, Zn, Fe, Ni, Co, Mo, Ti, Pt or their compounds. Also suitable are, for example, S, Se. phosphates of transition metals such as V and Fe, and heteropolyacids such as molybdophosphoric acid.

Examples of specific catalysts are:

sodium or sodium compounds (DE-A-37 19 055 and DE-A-38 11 509)

aluminum oxide, alkali metal aluminate and/or alkaline earth metal aluminate (EP-A04 05 348)

silver oxide (JP-A 60/089 441, Derwent Report 85 - 15 68 91126)

a catalyst comprising copper, zinc and sulfur (DE-A 25 25 174)

a catalyst comprising copper, zinc and selenium (U.S. Pat. No. 4,054,609)

a catalyst comprising zinc and/or indium (EP-A 0 130 068)

silver (U.S. Pat. No. 2,953,602)

silver, copper and silicon (U.S. Pat. No. 2,939,883)

compounds containing zinc, cadmium, selenium, tellurium or indium.

Preference is given to using sodium or sodium compounds.

The form in which such a catalyst, for example a sodium-containing catalyst, is used can vary widely: metallic, e.g. also as an alloy with at least one other alloy constituent, as compound or salt, where at least one nonmetallic element is chemically combined with Na (binary compounds and salts). If more than one element is present in chemically combined form in the compound, a binary, ternary or quaternary compound or salt is present. Use of the catalyst in supported form, for example on an inorganic support, is likewise preferred.

If sodium is used in metallic form, it can be used as solid, liquid or preferably as vapor. Preferred alloys are those with other alkali metals and/or alkaline earth metals, e.g. Ba, Sr, Ca, Cs, Rb, K or particularly preferably Li and/or magnesium.

Furthermore, alloys with B, Al, Si and Sn can also be used. This also applies, in particular, to alloys which can comprise compounds such as sodium boride $NaB_2$, sodium silicide NaSi or NaSn.

Examples of suitable binary sodium compounds and salts are sodium carbides such as $Na_2C_2$, $NaC_8$, sodium halides such as NaF, sodium oxides such as $Na_2O$, sodium azide, sodium phosphide, sodium sulfide, sodium polysulfides, preferably also sodium hydrides such as NaH.

Examples of suitable ternary sodium compounds and salts are sodium borates such as borax, sodium phosphates or hydrogenphosphates, sodium phosphites, sodium (meta) silicates and aluminosilicates, e.g. water glass, $Na_3AlF_6$ (cryolite), sodium (hydrogen)sulfate, sodium sulfite, sodium nitrite, sodium nitrate, sodium amide, sodium acetylide NaCCH, sodium cyanide, sodium thiocyanate, the sodium salt of methyl thiol, sodium thiosulfate, but preferably NaOR where R=H or an organic radical (=salts of organic acids, alkoxides, phenoxides, acetylacetonate, acetoacetic ester salt, salts of salicylic acid or of salicylaldehyde), sodium carbonate and sodium hydrogencarbonate and mixtures thereof, for example soda, thermonatrite, trona, pirssonite, natrocalcite. The use of anhydrous, I.e. dried, salts is generally preferred. Particular preference is given to NaOH, NaOOC-R⁻ (preferably formate, acetate, lactate, oxalate), NaOR' (R' is an organic radical having from 1 to 4 carbon atoms) and sodium carbide. Very particular preference is given to NaOH, sodium formate, sodium methoxide, sodium acetate and sodium carbides such as $Na_2C_2$.

Examples of suitable quaternary compounds are sodium-containing aluminosilicates which can be prepared synthetically or can also occur in a wide variety as natural minerals and rocks (e.g. sodium feldspar or laden and calcium-sodium feldspar or oligoclase). They can additionally be laden with Na by ion exchange.

Use can also advantageously be made of double salts of the alum type or thenardite, glauberite, astrakanite, glaserite, vanthoffite.

The sodium compounds and salts mentioned here can advantageously also be in the form of mixtures. In particular, it is quite possible to use contents of <50%, preferably <30%, of cations of other alkali metals and/or alkaline earth metals, e.g. Ba, Sr, Ca, Cs, Rb, K or preferably Li and/or magnesium. Industrially available, complex mixtures such as soda lime, ground basic slag and cements, e.g. Portland cement, if desired after enrichment with sodium by storage in sodium-containing solutions (NaCl, sea water) are particularly advantageous.

Particular preference is given to sodium compounds selected from the group consisting of:

a) sodium alkoxides, b) sodium carboxylates, c) sodium salts of C—H acid compounds, d) sodium oxide, sodium hydroxide, sodium nitrite, sodium acetylide, sodium carbide, sodium hydride and sodium carbonyl.

The abovementioned catalysts will hereinafter be referred to as primary catalyst.

In the process of the invention, the abovementioned compounds give formaldehyde yields of over 60% and low water concentrations of less than 5 mol % of $H_2O$ per mole of formaldehyde even at reaction temperatures of from 600 to 1000° C.

The liberation of the catalytically active species from the primary catalyst is preferably carded out by thermal decomposition of the latter.

The primary catalyst can, for example, be introduced initially or afterwards, in each case continuously or discontinuously, as solid, dissolved in a solvent, as a liquid or as a melt.

The subsequent introduction of the primary catalyst as a solid, e.g. in powder form, particulate or compacted, is generally carded out by means of solids metering, e.g. using a reciprocating or rotary piston, a cellular wheel feeder, a screw or a vibrating chute.

If the primary catalyst is added in dissolved form, particularly suitable solvents are those having a chemical composition consisting of only the elements already present in the process (C, H, O). particular preference is given to MeOH as solvent. The addition is carried out, for example, via a noble which can be cooled in order to avoid evaporation of the solvent or crystallization or deposition of the solid primary catalyst in the nozzle.

The addition of the primary catalyst as a melt can be carried out, for example, via a nozzle. The melt can then be vaporized or decomposed directly in the gas stream.

For all possible ways of introducing further primary catalyst, this is advantageously carded out in such a way that the material is in intimate contact with flowing gas. This can be achieved, for example, by applying the catalyst material by the above-described methods onto a suitable surface through or over which the gas flows. This can be the surface of a support material which is present in a fixed beds Suitable materials are, for example, SiC, $SiO_2$ and $Al_2O_3$ in a suitable geometric form, e.g. as granules, pellets or spheres. The support material is preferably arranged vertically in a fixed bed, preferably with metering-in from above. The substance which is introduced deposits on the support material and the catalytically active species goes into the gas phase during the process.

Another possibility is placing the primary catalyst in a fluidized bed through which the carrier gas stream is passed. Here, the fluidized material comprises at least some of the supported or unsupported primary catalyst. The loss of active substance can be made up by introducing further fresh primary catalyst; exhausted material can, if desired, be taken off. This can be realized in the continuous case, for example, by means of a circulating fluidized bed.

Further introduction of the primary catalyst can also be carried out by alternating secondary catalyst generation in different vessels in which the primary catalyst can be located, for example as a fixed bed or a fluidized bed, in each case supported or unsupported. The advantage of using a plurality of units for the discontinuous introduction of further catalyst is that it is also possible to use primary catalysts for which, e.g. owing to material properties such as melting point, viscosity or decomposition temperature, continuous feeding would be Impossible or possible only with great difficulty.

In a preferred variant of the process of the invention, the secondary catalyst is generated physically separately from the reaction zone in which the actual dehydrogenation takes place and at a temperature above the dehydrogenation temperature. The temperature difference between the site of catalyst generation and the reaction zone is preferably at least 20° C., particularly preferably from 40 to 250° C.

On thermal treatment of the primary catalysts according to the invention in the primary catalyst decomposition zone and on passing a reducing or non-reducing gas such as molecular nitrogen over them at temperatures which may be different from the reaction temperature for the dehydrogenation and may be higher or lower, one or more catalytically active species which are able to catalyze the dehydrogenation of methanol are released or generated and/or generated on them (secondary catalyst). Such a fluid catalyst can be transported over considerable distances without suffering an appreciable loss of effectiveness in the dehydrogenation. This separate setting of temperatures makes it possible, in particular, to lower the reaction temperature by matching to the respective conditions for catalyst liberation/vaporization or generation of a catalytically active species (secondary catalysts on the one hand and to the reaction on the other hand. This reduces the decomposition of the formaldehyde, which is unstable under the reaction conditions, as a result of secondary reactions and increases the yield.

Preferred temperatures for generating the secondary catalyst from the primary catalyst are from 300 to 1100° C., particular preference is given to temperatures of from 400 to 1000° C.

In addition, the residence times in the dehydrogenation reactor and vessels for primary catalyst addition or for penetrating the secondary catalyst can be set separately by dividing the carrier gas stream. This achieves a targeted loading of the gas stream passed through the catalyst addition unit with the active species.

Preferred residence times for generating the secondary catalyst are from 0.01 to 60 sec, particularly preferably from 0.05 to 3 sec.

Commercial methanol can be used for the reaction; it should preferably be low in water and contain no substances which poison the catalyst.

To carry out the dehydrogenation, the fluid, preferably gaseous, methanol is preferably diluted with carrier gas.

The molar proportion of methanol is generally from 5 to 90%, preferably from 10 to 50%, particularly preferably from 10 to 40%.

The pressure is not critical in the process of the invention. The dehydrogenation of the methanol can be carried out at subatmospheric pressure, atmospheric pressure or subatmospheric pressure. A range from about 0.1 to 10 bars preferably from 0.5 to 2 bar, is particularly suitable. Preference is given to atmospheric pressure. The process of the invention can be carried out discontinuously or continuously, with the latter being preferred. The temperature is generally from 300° C. to 950° C., preferably from 500 to 900° C., particularly preferably from 600 to 850° C.

If the secondary catalyst is generated physically separately from the reaction zone, the temperatures in the reaction zone are generally from 200 to 1000° C., preferably from 300° C. to 980° C. Preference is given to reacting from 0.01 to 1 kg of methanol per hour and per gram of catalyst used. In the case of a continuous process, further catalyst has to be introduced continuously or discontinuously. The amounts here are generally from 10 milligrams to 5 grams, preferably from 10 mg to 1 g, particularly preferably from 50 to 1000 mg, very particularly from 50 mg to 500 mg. per kg of methanol reacted.

For the dehydrogenation of the methanol, residence times in the reaction zone are preferably from 0.005 to 30 sec, particularly preferably from 0.01 to 15 sec, very particularly preferably from 0.05 to 3 sec.

Suitable reactors are well known to those skilled in the art. Essentially, it is possible to use reactor types and assemblies as are known from the literature for dehydrogenation reactions. Such apparatuses are described, for example, in Winnacker/Küchler, Chemische Technologie, 4th edition, chapter "Technik der Pyrolyse" Hanser Verlag, Munich 1981–86. Suitable reactors are, for example, tube reactors; suitable reactor materials are, for example, ceramic materials such as α-alumina but also iron- and nickel-based alloys which are resistant to carbonization, heat and scale, e.g. Inconel 600® or Hasteloy®.

If the reactor 5 or the vessel 2 is heated by means of a combustion reaction, eternally fired tubes, for example, are suitable.

Preference is likewise given to heating the reactor by means of microwaves.

In a further preferred variant of the process of the Invention, a circulating gas stream consisting essentially of by-products of the dehydrogenation is passed through the reactor, Preference is also given to bleeding off part of the by-products from the circulating gas process and using this for firing the reactor.

The formaldehyde can be separated from the reaction mixture by methods known per se with which those skilled in the art are familiar, for example by polymerization, condensation or physical or chemical absorption or adsorption.

An industrially proven method is the formation of hemiacetals from formaldehyde and an alcohol. The hemiacetals are subsequently dissociated thermally, giving very pure formaldehyde vapor. The alcohol used is usually cyclohexanol since its boiling point is sufficiently far above the decomposition temperature of the hemiacetal. The hemiacetals are usually dissociated in failing film or thin film evaporators at temperatures of from 100 to 160° C. (see, for example, U.S. Pat. No. 2,848,500 of Aug. 19, 1958 "Preparation of Purified Formaldehyde" and U.S. Pat. No. 2,943, 701 of Jul. 5, 1960 "Process for purification of gaseous formaldehyde", or JP-A 62/289 540). The formaldehyde vapors which are liberated in such a process still contain small amounts of impurities which are usually removed by means of a countercurrent scrub using alcohol such as cyclohexanol hemiformal, by condensation or also by targeted prepolymerization.

Particularly preferred methods of purifying the formaldehyde prepared according to the invention are described in the German Patent Applications 19 747 647.3 and 19 748 380.1.

A further method of separating formaldehyde from the reaction mixture is the formation of trioxane in a catalytic gas-phase process (see, for example, Appl. Catalysis A 1997, 150, 143–151 and EP-A 0 691 338). Trioxane can then, for example, be condensed out.

Possible uses of the by-products of the reaction, in particular hydrogen, are, for example, the synthesis of methanol or the isolation of pure hydrogen which can be separated off, for example, by means of membranes.

Hydrogen obtained in this way is suitable, for example, for the synthesis of ammonia, in refinery processes for producing gasoline and petrochemical cracking products, for the synthesis of methanol, for hardening fats and for other hydrogenations, as reducing agent for producing W, Mo, Co and other metals, as reducing protective gas in metallurgical processes, for autogenous welding and cutting, as fuel gas in admixture with other gases (town gas, water gas) or in liquefied form as fuel in aerospace applications.

The formaldehyde prepared by the process of the invention is suitable for all known fields of application, for example corrosion protection, production of mirrors, electrochemical coatings, for disinfection and as a preservative, likewise as an intermediate for producing polymers, for example polyoxymethylenes, polyacetals, phenolic resins, melamines, aminoplastics, polyurethanes and casein plastics, and also 1,4-butanol, trimethylolpropane, neopentyl glycol, pentaerythritol and trioxane, for methanolic formaldehyde solutions and methylal, for producing dyes such as fuchsin, acrydine, for producing fertilizers and for treating seed.

Since the process of the invention usually produces formaldehyde having a low water content, formaldehyde prepared in this way is particularly suitable for polymerization to give polyoxymethylene and trioxane, since water-free formaldehyde has to be used for this purpose.

The invention also relates to plastics such as polyoxymethylene and polyacetals, trioxane, dyes, fertilizers and seed produced in such a way.

The invention further provides a process for preparing trioxane, which comprises
 1. converting methanol into formaldehyde by dehydrogenation in a reactor at a temperature in the range from 300 to 1000° C. in the presence of a catalyst, where a carrier gas stream having a temperature above the dehydrogenation temperature is fed to the reactor, and
 2. the formaldehyde prepared in this way is trimerized to give trioxane.

Details of the preparation of trioxane are well known to those skilled in the art. They are described, for example, in Kirk-Othmer, Encyclopedia of Chemical Technology, 2nd edition, volume 10, pp. 83, 89, New York Interscience 1963–1972.

The invention likewise provides a process for preparing polyoxymethylene, which comprises
 1. converting methanol into formaldehyde by dehydrogenation in a reactor at a temperature in the range from 300 to 1000° C. in the presence of a catalyst, where a carrier gas stream having a temperature above the dehydrogenation temperature is fed to the reactor, and
 2. if desired, purifying the formaldehyde obtained in this way,
 3. polymerizing the formaldehyde,
 4. capping the end groups of the polymer prepared in this way and
 5. if desired, homogenizing the polymer in the melt and/or providing it with suitable additives.

The preparation of polyoxymethylene from formaldehyde is well known to those skilled in the art. Details may be found, for example, in Ullmann's Encyclopedia of Industrial Chemistry, volume 21, 5th edition, Weinheim 1992, and the literature cited therein.

The invention further provides a process for preparing polyoxymethylene copolymers, which comprises
 1. converting methanol into formaldehyde by dehydrogenation in a reactor at a temperature in the range from 300 to 1000° C. in the presence of a catalyst, where a carrier gas stream having a temperature above the dehydrogenation temperature is fed to the reactor, and
 2. trimerizing the formaldehyde obtained in this way to give trioxane,
 3. if desired, purifying the trioxane,
 4. copolymerizing the trioxane with cyclic ethers or cyclic acetals,
 5. if desired, removing unstable end groups and
 6. if desired, homogenizing the polymer prepared in this way in the melt and/or admixing if with suitable additives.

The invention further provides a process for preparing polyoxymethylene copolymers, which comprises
 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and
 2. if desired, purifying the formaldehyde obtained in this way,
 3. copolymerizing the formaldehyde with cyclic ethers or cyclic acetals,
 4. if desired, removing unstable end groups and
 5. if desired, homogenizing the polymer prepared in this way in the melt and/or admixing it with suitable additives.

The preparation of polyoxymethylene copolymers is well known to those skilled in the art. Details may be found, for example, in Ullmann's Encyclopedia of Industrial Chemistry, volume 21, 5th edition, Weinheim 1992 and the literature cited therein, and also in the Russian documents SU 436067, 740715 and SU 72-1755156, 720303.

The contents of the priority-establishing German Patent. Applications 197 22 774.0, 197 27 519.2 and 19743145.3 and also the Abstract of the present application are expressly incorporated by reference into the present description.

The invention is illustrated by the examples without being restricted thereby.

EXAMPLES

Figure 2:
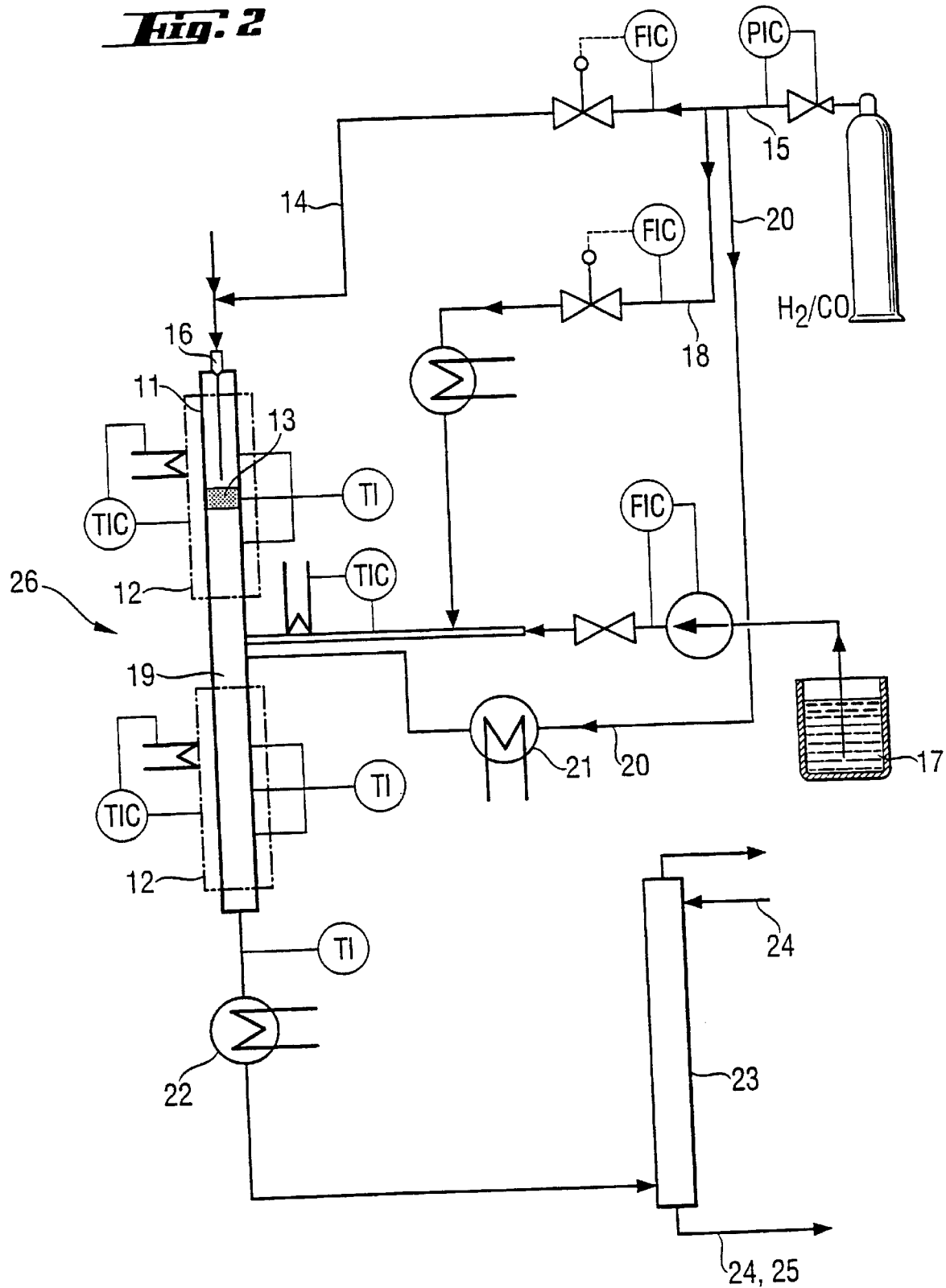

FIG. 2 schematically shows the configuration of the experimental apparatus by means of a flow diagram.

The dehydrogenation of the methanol is carried out in a tube reactor 26 which is indirectly heated by means of an electric tube furnace 12. A catalyst addition unit is formed by a metal tube 11 which is indirectly heated by the electric tube furnace 12. In the tube 11, there is a bed 13 of support material on which the primary catalyst (0.1–5.0 g) is located. A part 14 of a superheated carrier gas stream 15 which has been preheated beforehand by means of heated feed lines is introduced into this tube 11. In addition, further primary catalyst is fed as a solution via a nozzle 16 into this tube 11. The primary catalyst deposits on the bed 13. The carrier gas substream 14 is passed through the bed in order to load the carrier gas substream with an active catalyst species which forms. The total stream is subsequently introduced into the reaction space 19.

Methanol 17 is preheated, conveyed in a further part 18 of the carrier gas stream 15 and likewise introduced into the reaction space 19.

A third gas stream 20 consisting of pure carrier gas 15 is superheated 21, i.e. brought to a temperature which is above the dehydrogenation temperature, and likewise introduced into the reaction space 19.

The reaction space 19 is formed by a tube having a length of 200–450 mm, internal diameter 4–21 mm. In a cooler 22, the product gases leaving the reaction space 19 are quickly cooled to a temperature below 200° C. and are analyzed by means of a gas chromatograph. In a column 23, the reaction products are scrubbed with alcohol 24 (e.g. cyclohexanol at 20–80° C.) in order to remove the formaldehyde 25. The primary catalyst used is sodium methoxide, the carrier gas used is $H_2/CO$ or nitrogen. The total flow is 20–500 l/h, at least 50% of the carrier gas stream is fed directly to the reactor after superheating. The methanol feed rate is such that a methanol concentration of about 520 mol % is established.

The formaldehyde yield is calculated as follows.

$$\text{Yield (in \%)} = \frac{\text{formaldehyde formed (mol)}}{\text{methanol fed in (mol)}} \cdot 100$$

| Example/ Comparative Example | Furnace temperature for catalyst decomposition | Temperature of carrier gas stream | Furnace temperature for reactor, dehydrogenation | Yield of formaldehyde |
|---|---|---|---|---|
| Example 1 | 900° C. | 870° C. | 750° C. | 76% |
| Example 2 | 880° C. | 870° C. | 750° C. | 74% |
| CE 1 | 900° C. | 820° C. | 750° C. | 72% |

What is claimed is:

1. A process for preparing formaldehyde from methanol by dehydrogenation in a reactor in the presence of a catalyst at a temperature in the range from 300 to 1000° C., wherein a carrier gas stream which has a temperature above the dehydrogenation temperature is fed to the reactor.

2. The process as claimed in claim 1, wherein the temperature difference is at least 20° C.

3. The process as claimed in claim 1, wherein the catalyst is generated physically separately from the reactor.

4. The process as claimed in claim 1, wherein a primary catalyst is used for generating the catalyst and further amounts of this primary catalyst are introduced continuously.

5. The process as claimed in claim 1, wherein the carrier gas steam consists essentially of the by-products of the dehydrogenation.

6. The process as claimed in claim 1, wherein part of the by-products of the dehydrogenation is used as fuel for heating the reactor.

7. The process as claimed in claim 1, wherein the hydrogen formed as by-product is separated off.

8. The process as claimed in claim 1, wherein the catalyst used is one or more sodium compounds which are selected from the group consisting of:
   sodium alkoxides,
   sodium carboxylates,
   sodium salts of C—H acid compounds,
   sodium oxide, sodium hydroxide, sodium nitrite, sodium acetylide, sodium carbide, sodium hydride and sodium carbonyl.

9. A process as claimed in claim 1 for preparing formaldehyde from methanol by dehydrogenation of the methanol at a temperature in the range from 300 to 1000° C. in the presence of a catalytically active species set free from a sodium compound, wherein the sodium compound used is:
   a) sodium alkoxides,
   b) sodium carboxylates,
   c) sodium salts of C—H acid compounds or
   d) sodium oxide, sodium hydroxide, sodium nitrite, sodium acetylide, sodium carbide, sodium hydride or sodium carbonyl.

10. The process as claimed in claim 9, wherein the sodium compound used is
    a) sodium alkoxides of lower ($C_1$–$C_6$)alcohols or glycolates;
    b) sodium carboxylates of lower ($C_1$–$C_6$)monocarboxylic, dicarboxylic, tricarboxylic or hydroxylcarboxylic acids;
    c) sodium acetylacetonate or sodium salt of ethyl acetoacetate or
    d) sodium carbide.

11. The process as claimed in claim 10, wherein the sodium compound used is
    a) $NaOCH_3$, $NaOC_2H_5$ or $NaO-(CH_2)_2-ONa$ or
    b) NaOOCH, $NaOOC-CH_3$, $NaOOC-C_2H_5$ or $NaOOC-CH(OH)-CH_3$;
    c) $Na_2C_2$.

12. The process as claimed in claim 11, wherein the sodium compound used is $NaOCH_3$, NaOOCH, $NaOOC-CH_3$ and/or $Na_2C_2$.

13. The process as claimed in claim 9, wherein the sodium compound is fed in, or further amounts are fed in, as a solid, as a solution in a solvent, as a liquid or as a melt, in each case continuously or discontinuously.

14. The process as claimed in claim 13, wherein the dehydrogenation is carried out in a reactor and the generation of the catalytically active species is carried out physically separately from the reactor.

15. The process as claimed in claim 9, wherein the dehydrogenation is carried out in a reactor and a circulating gas steam which consists essentially of by-products from the dehydrogenation is passed through the reactor.

16. The process as claimed in claim 9, wherein the dehydrogenation is carried out in a reactor and part of the by-products of the dehydrogenation are used as fuel for heating the reactor.

17. The process as claimed in claim 9, wherein the methanol is diluted with a carrier gas and the carrier gas stream is heated before it is combined with the methanol.

18. The process as claimed in claim 9, wherein the hydrogen obtained as by-product is separated off and passed on to a further use.

* * * * *

UNITED STATES PATENT AND TRADEMARK OFFICE
CERTIFICATE OF CORRECTION

PATENT NO. : 6,339,175 B1  
DATED : January 15, 2002  
INVENTOR(S) : Elke Schweers, Thomas Kaiser, Michael Haubs and Michael Rosenberg It is certified that error appears in the above-identified patent and that said Letters Patent is hereby corrected as shown below:

<u>Title page,</u>  
The title should read as -- METHOD FOR PRODUCING FORMALDEHYDE FROM METHANOL IN A NON-OXIDATING MANNER --.

<u>Column 3,</u>  
Line 27, delete "911126" and insert -- 91/26 --.

<u>Column 4,</u>  
Line 53, delete "carded" and insert -- carried --.  
Line 67, delete "particular" and insert -- Particular --.

<u>Column 5,</u>  
Line 2, delete "noble" and insert -- nozzle --.  
Line 9, delete "carded" and insert -- carried --.

<u>Column 9,</u>  
Line 47, delete "520" and insert -- 5-20 --.

Signed and Sealed this

Seventeenth Day of December, 2002

JAMES E. ROGAN  
*Director of the United States Patent and Trademark Office*